US00PP18572P3

(12) United States Plant Patent
Yencho et al.

(10) Patent No.: US PP18,572 P3
(45) Date of Patent: Mar. 11, 2008

(54) ORNAMENTAL SWEETPOTATO PLANT NAMED 'SWEET CAROLINE SWEETHEART LIGHT GREEN'

(50) Latin Name: *Ipomoea batatas*
Varietal Denomination: Sweet Caroline Sweetheart Light Green

(75) Inventors: George Craig Yencho, Raleigh, NC (US); Kenneth Pecota, Raleigh, NC (US); Charles Newell Hancock, Bear Creek, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/395,060

(22) Filed: Mar. 31, 2006

(65) Prior Publication Data

US 2007/0143896 P1 Jun. 21, 2007

Related U.S. Application Data

(60) Provisional application No. 60/752,486, filed on Dec. 21, 2005.

(51) Int. Cl.
*A01H 5/00* (2006.01)

(52) U.S. Cl. ..... Plt./258

(58) Field of Classification Search ..... Plt./258
See application file for complete search history.

(56) References Cited

U.S. PATENT DOCUMENTS

2007/0143896 P1 * 6/2007 Yencho et al. ..... Plt./258

* cited by examiner

*Primary Examiner*—Wendy C. Haas
*Assistant Examiner*—Georgia Helmer
(74) *Attorney, Agent, or Firm*—Myers Bigel Sibley & Sajovec P.A.

(57) ABSTRACT

*Ipomoea batatas* 'Sweet Caroline Sweetheart Light Green' is a very compact to compact, partially mounded cultivar producing many shoots and having dense foliage. This cultivar is distinguishable from other cultivars by small, heart-shaped, light green to chartreuse colored leaves and erect to semi-erect architecture. The plant has good vigor, is very well branched, and has thin stems that tend to intertwine. It is much less vigorous than *Ipomoea batatas* 'Margarita' and 'Blackie', and is well suited for container production. The production of flowers by 'Sweet Caroline Sweetheart Light Green' is are even under short day conditions.

2 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the varietal denomination 'Sweet Caroline Sweetheart Light Green'.

BACKGROUND OF THE INVENTION

*Ipomoea* species are members of the morning glory family Convolvulaceae. *Ipomoea batatas,* the cultivated species, is commonly produced for consumption and referred to as the white or yellow sweetpotato and the orange yam. The plants are typically fast growing, green vines possessing a wide variety of leaf shapes ranging from palmate and deeply lobed, to cordate or triangular shaped leaves with no lobes. Ornamental sweetpotates, which have been bred and selected for their unique foliage colors, leaf shapes and plant habits, typically do not produce large fleshy storage roots like the sweetpotato cultivated for consumption. In comparison, storage roots produced by ornamental sweetpotates are typically not as large because no selection has been exercised for yield, thus storage roots do not begin to swell until very late in the season. Further, the few storage roots that are formed by ornamental sweetpotatoes are typically not as attractive as those produced by the table-stock types as they are generally cracked, very malformed, often mottled in skin and flesh color, and are not palatable.

Late in the growing season when day-lengths begin to shorten or when the plants are stressed, ornamental sweetpotato plants produce tubular flowers that are similar to morning glories, but most plantings are dominated by the appearance of the foliage. The plants are highly desirable due to their ability to grow under varied stress conditions, cover a large space, and last the entire growing season. Moreover, these plants have few insect or disease problems.

Until the release of the Sweet Caroline series of ornamental sweet potatoes (see below) there were six popular types of *Ipomoea batatas* ornamental sweetpotates being cultivated primarily for their annual, summer vines in landscaping applications. These six cultivars are: 'Blackie' (not patented), having purple foliage and lavender flowers; 'Terrace Lime' (not patented) and 'Margarita' (not patented; also known as 'Sulfur'), which have large brilliant chartreuse leaves and lavender blooms; 'Black Heart' (not patented; also known as 'Ace of Spaces'), having heart-shaped leaves with burgundy purple color; 'Tricolor' (not patented; also known as 'Pink Frost'), a variegated plant having plate green, white, and pink-margined leaves; and 'Lady Fingers' (unpatented), which has medium green, dainty leaves divided into long, thin, fingerlike lobes that are complemented by burgundy stems and veins.

*Ipomoea batatas* 'Margarita' was recently been released in the United States, and has become widely used as a landscape annual. However, it is not suitable for mixed containers as this variety exhibits a very vigorous growth and tends to out-compete other species. See Armitage. A. M. and J. M. Garner, (2001) *Ipomoea batatas* 'Margarita'. HortScience 36:178. Another popular variety, 'Blackie', is a vigorous purple-leaved clone, which is also unsuited to containerized gardens.

Therefore, to meet the current horticultural demand, it is desirable to produce new, more robust cultivars of ornamental sweetpotato with attractive foliage colors, leaf shapes, and plant architectures. In addition, it would be advantageous to develop cultivars of ornamental sweetpotato exhibiting a more compact growth, and which do not out-compete other species in mixed containers.

*Ipomoea batatas* 'Sweet Caroline Light Green' (U.S. Plant Pat. No. 15,028, issued Jul. 20, 2004), 'Sweet Caroline Green' (U.S. Plant Pat. No. 15,056, issued Aug. 3, 2004), 'Sweet Caroline Bronze' (U.S. Plant Pat. No. 15,437, issued Dec. 21, 2004), 'Sweet Caroline Purple' (U.S. Plant Pat. No. 14,912, issued Jun. 15, 2004), and 'Sweet Caroline Red' (U.S. Plant Pat. No. 17,483, issued Mar. 13, 2007) are recently introduced cultivars developed at North Caroline State University that are characterized by compact growth habit, moderate to deeply lobed palmate leaves, and attractive foliage color.

The present invention relates to a new and distinct variety of *Ipomoea batatas* named 'Sweet Caroline Sweetheart Light Green'. 'Sweet Caroline Sweetheart Light Green' is a very compact to compact, partially mounded variety producing many shoots and having dense foliage. This variety is distinguishable from other varieties by its small, heart-shaped, light green to chartreuse colored leaves and erect to semi-erect architecture. The plant has good vigor, is very well branched, and has thin stems that tend to intertwine. It is much less vigorous than *Ipomoea batatas* 'Margarita' and 'Blackie' and is well suited for container production.

Lineage. The *Ipomoea batatas* 'Sweet Caroline Sweetheart Light Green' cultivar (breeding designation NC779-23NORN) originated from a conventional cross between *Ipomoea batatas* cultivars NC7-1ORN (the female parent; not patented) and NC146-1ORN (the male parent; not patented) conducted during October 2001 to April 2002 at Raleigh, N.C.

NC7-1ORN was selected from seed obtained from the selfing of 'Sulfur'. NC146-1ORN resulted from a cross between 'Sulfur' (the female parent) and the clone 'S×BLR7-2' (the male parent; not patented). 'S×BLR7-2' was derived from a cross between 'Sulfur' (the female parent) and 'Blackie' (the male parent). Seed from this cross were planted in the Horticultural Greenhouses in Spring 2002. The single, individual plant now known as *Ipomoea batatas* 'Sweet Caroline Sweetheart Light Green' was selected in August and September 2002 because of its combination of exceptional features, and has been propagated asexually since that time.

Asexual Reproduction. Since its selection, *Ipomoea batatas* 'Sweet Caroline Sweetheart Light Green' has been asexually reproduced at Raleigh, N.C., predominantly by vegetative propagation of vine cuttings. Successively, there have been three cycles of vegetative propagation, one cycle of tissue culture micropropagation, and multiple vegetative propagation cycles to increase the plant population. Asexual reproduction of the new Ornamental Sweetpotato cultivar by cuttings has shown that the unique features of the new cultivar are stable and the plant reproduces true to type in successive generations of asexual reproduction.

SUMMARY OF THE INVENTION

*Ipomoea batatas* 'Sweet Caroline Sweetheart Light Green' is a very compact to compact, partially mounted cultivar producing many shoots and having dense foliage. This cultivar is distinguishable from other cultivars by small, heart-shaped, light green to chartreuse colored leaves and erect to semi-erect architecture. The plant has good vigor, is very well branched, and has thin stems that tend to intertwine. It is much less vigorous than *Ipomoea batatas* 'Margarita' and 'Blackie', and is well suited for container production. The production of flowers by 'Sweet Caroline Sweetheart Light Green' is rare even under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION

Figure 1:
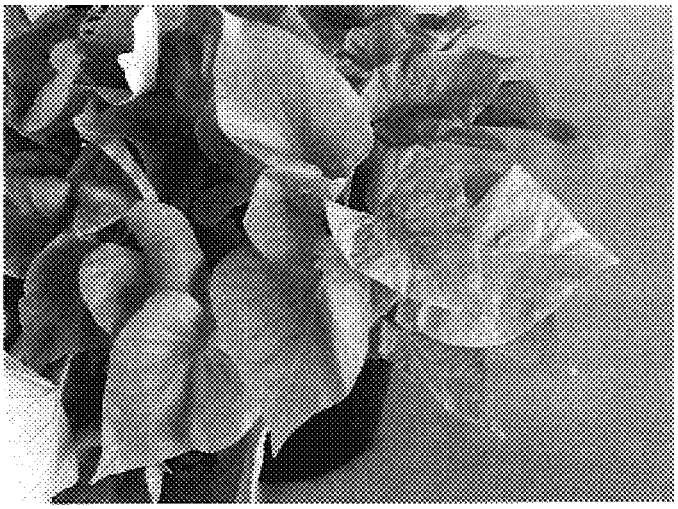
FIG. 1 is a color photograph showing both new and mature foliage produced by variety *Ipomoea batatas* 'Sweet Caroline Sweetheart Light Green'. The plant shown in FIG. 1 is 11 weeks of age.
Figure 2:
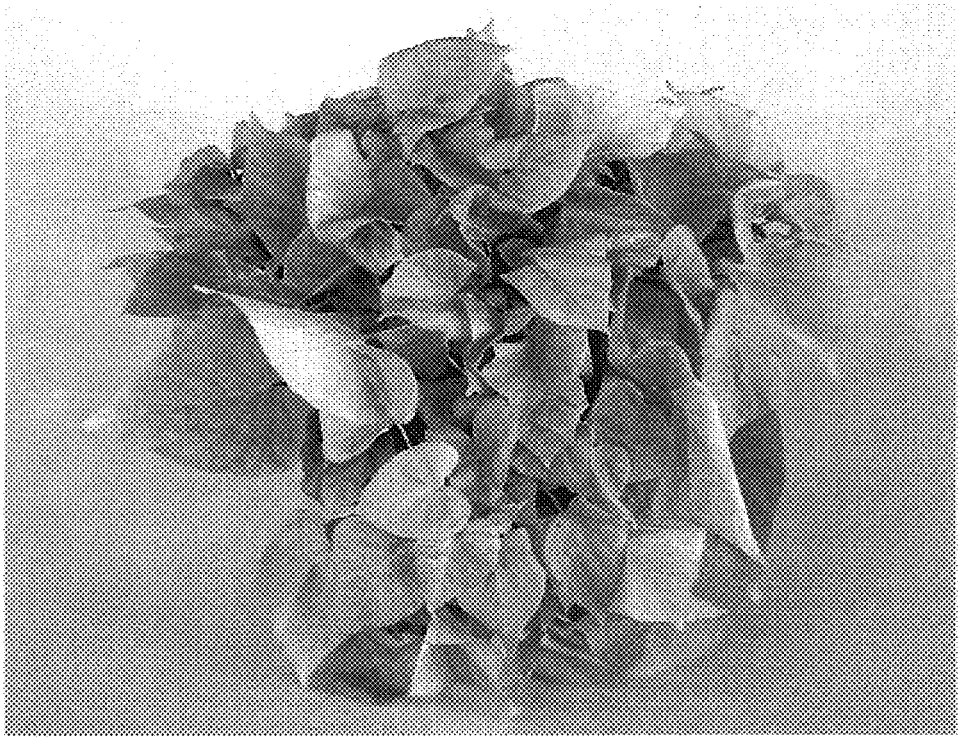
FIG. 2 is a color photograph showing a typical plant of the variety *Ipomoea batatas* 'Sweet Caroline Sweetheart Light Green'. The plant shown in FIG. 2 is 11 weeks of age.

The following is a detailed description of the botanical characteristics of the new and distinct cultivar of *Ipomoea batatas* plant known by the cultivar name 'Sweet Caroline Sweetheart Light Green'. All colors cited herein refer to The Royal Horticultural Society Colour Chart (The Royal Horticultural Society, London, 1995 edition) designations except where general terms of ordinary dictionary significance are used. Where dimensions, sizes, colors, and other characteristics are given, it is to be understood that such characteristics are approximations or averages set forth as accurately as practicable.

The descriptions reported herein are from 11-week-old specimens. *Ipomoea batatas* 'Sweet Caroline Sweetheart Light Green' has not been observed under all possible environmental conditions; therefore, the phenotype may vary under different environmental conditions such as season, temperature, light intensity, day length, cultural conditions, and the like, without however any variance in the genotype.

Technical Description of the Variety.

Above-Ground Structure. *Ipomoea batatas* 'Sweet Caroline Sweetheart Light Green' is a very compact to compact, partially mounded cultivar. Plant height is 20 cm and area of spread is 43 cm. It is a moderately fast grower with good vigor. The foliage is very dense due to many leaves and results in a round uniform plant habit.

Branching habitat. Free branching with no basal shoots.

Lateral shoots. The number of lateral shoots varies but averages around 6 with multiple short secondary shoots.

Lateral branch length: about 28 cm. Diameter: about 0.4 cm. Internode length: about 1.5 cm. Stems are round, smooth and sturdy without any pubescence. Shoots are initially upright but then fall outward, forming a dense canopy. Color: bright yellow-green (RHS 145B).

Petiole. Leaf petiole length varies with an average of 5.5 cm. Diameter: 0.25 cm. Petiole texture is smooth. Color is 144B above and below.

Foliage. Leaves are alternate and tend to spiral around the stems. They are simple and heart-shaped (cordate). The number of leaves per stem varies with length but an average stem has about 30 leaves. The leaf tip is acuminate and the base is cordate. Leaf margins are entire and the leaves are smooth and mat with not pubescence. Leaf length averages 8.8 cm (up to 11.2 cm) and leaf width averages 7.4 cm (up to 9 cm). Young leaves are a little puckered and sinuate but flatten into decorative hearts as they mature. The venation pattern is palmate at the leaf base becoming arcuate toward the leaf tip. Color: see Table. 1.

TABLE 1

| Leaf Structure | Upper Surface | Lower Surface |
|---|---|---|
| Young Leaf | Bright green, RHS 145A | Bright green, a little more grey than RHS 145A |
| Mature Leaf | Bright yellow-green, RHS 144C | Bright yellow-green, more grey than RHS 145B |
| Vein | 144C | 144D |

Flowers. The production of flowers by 'Sweet Caroline Sweetheart Light Green' is very rare even under short day conditions and when produced the flowers are ephemeral (in most cases open only in the morning). Thus, despite best efforts, no flowers have been available for use in providing a description or photographs.

Figure 3:
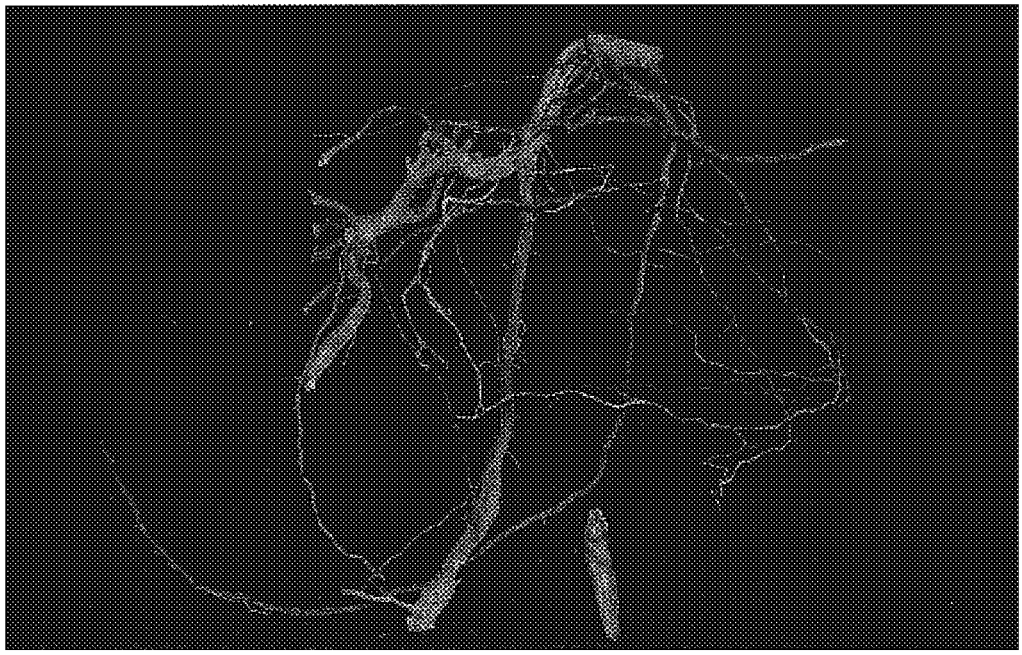
FIG. 3 is a color photograph showing typical storage roots produced by *Ipomoea batatas* 'Sweet Caroline Sweetheart Light Green' 123 days after planting. Plants were planted as five-hill plots spaced 30.5 cm apart in the row at the Horticultural Crops Research Station, Clinton, N.C. USA.

Below-Ground Structure. Plants form no, to very small, underground storage roots that are highly malformed and do not meet USDA Sweetpotato Storage Root Grade Standards (FIG. 3). Storage roots that do form typically possess rose colored skin (186A) with a cream colored flesh that quickly oxidizes to a light green color (191A).

Growth Conditions. *Ipomoea batatas* 'Sweet Caroline Sweetheart Light Green' has moderate vigor and a slow to moderate growth rate. It is very adaptable to container culture. In locales with mild winter conditions, *Ipomoea batatas* 'Sweet Caroline Sweetheart Light Green' will grow perennially; otherwise it is an annual plant. Similar to cultivated sweetpotatoes, wind or rain rarely causes much damage to 'Sweet Caroline Sweetheart Light Green', but if damage does occur, the plant drops the damaged leaves and grows new shoots at nodes where the leaves were lost.

Disease or Pest Resistance. *Ipomoea batatas* 'Sweet Caroline Sweetheart Light Green' is susceptible to Sweetpotato Feathery Mottle Virus and damage by Japanese beetles.

Comparison with Other *Ipomoea batatas* Cultivars.

'Sweet Caroline Sweetheart Light Green' is very distinct based on leaf color, leaf shape and plant architecture (Table 2). Of the most common cultivars of ornamental sweetpotato, *Ipomoea batatas* 'Sweet Caroline Sweetheart Light Green' is best compared with the 'Margarita' and 'Terrace Lime' cultivars. Like 'Margarita' (not patented) and 'Terrace Lime' (not patented), *Ipomoea batatas* 'Sweet Caroline Light Green' has light yellow-green to chartreuse leaves. However, where 'Margarita' and 'Terrace Lime' have large, slightly-lobed leaves, 'Sweet Caroline Sweetheart Light Green' has small, heart-shaped leaves. Moreover, 'Sweet Caroline Sweetheart Light Green' has a very compact to compact plant habit and strong tendency to intertwine as compared with the trailing habit of 'Margarita'.

The parental strains used to produce 'Sweet Caroline Sweetheart Light Green' were NC7-1ORN (female parent) and NC146-1ORN (male parent). NC7-1ORN is a moderately vigorous, moderately compact, moderately branched plant with medium sized heart-shaped to slightly lobed leaves that are light green in color, NC146-1ORN is a moderately vigorous, trailing, moderately branched plant with medium sized heart-shaped leaves that are greenish-bronze in color.

TABLE 2

| Characteristic | New Variety 'Sweet Caroline Sweetheart Light Green' | Comparison 1 'Margarita' | Comparison 2 'Terrace Lime' |
|---|---|---|---|
| Plant Habit | Very Compact to Compact | Trailing | Trailing |
| Foliage Color | Light Green to Yellow | Light Green to Yellow | Light Green to Yellow |
| Leaf Size | Small | Moderate to Large | Moderate to Large |
| Leaf Shape | Heart-shaped | Slightly Lobed | Slightly Lobed |
| Stem Thickness | Very Thin | Moderately Thick | Moderately Thick |

What is claimed is:

1. A new and distinct cultivar of *Ipomoea batatas* plant named 'Sweet Caroline Sweetheart Light Green', substantially as illustrated and described herein.

* * * * *

UNITED STATES PATENT AND TRADEMARK OFFICE

CERTIFICATE OF CORRECTION

PATENT NO. : PP 18,572 P3
APPLICATION NO. : 11/395060
DATED : March 11, 2008
INVENTOR(S) : Yencho et al.

It is certified that error appears in the above-identified patent and that said Letters Patent is hereby corrected as shown below:

On the Title Page:
In the Abstract:
Item 57, Line 11: Please correct "is are even"
To read -- is rare even --

Signed and Sealed this

First Day of July, 2008

JON W. DUDAS
*Director of the United States Patent and Trademark Office*